United States Patent [19]
Salzstein et al.

[11] Patent Number: 5,163,962
[45] Date of Patent: Nov. 17, 1992

[54] COMPOSITE FEMORAL IMPLANT HAVING INCREASED NECK STRENGTH

[75] Inventors: Richard A. Salzstein, Wilmington, Del.; Guy R. Toombes, Salt Lake City, Utah

[73] Assignee: BHC Laboratories, Inc., Wilmington, Del.

[21] Appl. No.: 574,684

[22] Filed: Aug. 30, 1990

[51] Int. Cl.$^5$ ............................................. A61F 2/32
[52] U.S. Cl. ........................................ 623/23; 623/66
[58] Field of Search .................. 623/11, 16, 18, 20, 623/22, 23, 66

[56] References Cited

U.S. PATENT DOCUMENTS

| | | |
|---|---|---|
| 4,221,623 | 9/1980 | Heissler et al. ............... 623/18 |
| 4,411,027 | 10/1983 | Alexander et al. ............ 623/18 |
| 4,459,708 | 7/1984 | Buttazzoni .................... 623/18 |
| 4,506,681 | 3/1985 | Mundell . |
| 4,512,038 | 4/1985 | Alexander et al. . |
| 4,662,887 | 5/1987 | Turner et al. . |
| 4,714,467 | 12/1987 | Lechner et al. ............... 623/23 |
| 4,738,681 | 4/1988 | Koeneman et al. . |
| 4,750,905 | 6/1988 | Koeneman et al. ........... 623/23 |
| 4,778,469 | 10/1988 | Lin et al. . |
| 4,892,552 | 1/1990 | Ainsworth et al. ............ 623/23 |
| 4,902,297 | 2/1990 | Deuanathan ................... 623/23 |

FOREIGN PATENT DOCUMENTS 0277727 8/1988 European Pat. Off. .
2104009 4/1972 France .
2350825 12/1977 France .
WO8504323 10/1985 World Int. Prop. O. .

OTHER PUBLICATIONS

Gregory Born McKenna, "The Development of Fiber Reinforced Polymer Composites for Orthopedic Applications," Xerox University Microfilms, Ann Arbor, Michigan, 1976, pp. 1–36.
Kenneth R. St. John, "Applications of Advanced Composites in Orthopaedic Implants," Biocompatible Polymers, Metals, and Composites, Technomic Publishing Co. Inc., Lancaster, PA, 1983, pp. 861–871.

Primary Examiner—David Isabella
Attorney, Agent, or Firm—Wegner, Cantor, Mueller & Player

[57] ABSTRACT

Disclosed is an improvement in a femoral implant for a hip prosthesis involving a longitudinal shaft having a neck extending therefrom at an acute angle $\theta$ to the longitudinal direction made of layers of carbon fiber in a polymeric matrix, each layer containing unidirectional fibers and the layers arranged such that carbon fibers are oriented in the longitudinal direction and the $\pm\theta$ direction. The improvement involves balancing at least 50% of the layers in the $\pm\theta$ direction.

14 Claims, 3 Drawing Sheets

COMPOSITE FEMORAL IMPLANT HAVING INCREASED NECK STRENGTH

The present invention relates to a femoral implant used in a hip-joint prosthesis. In particular, the invention relates to implants made of composite laminates of continuous carbon fiber in a polymeric matrix.

A femoral implant, as the name implies, replaces the end of a femur in a hip-joint prosthetic device. The femoral implant basically includes a longitudinal stem or shaft, which sits in a cavity formed in the proximal region of the femur, and a neck that extends from the shaft terminating in a ball, which cooperates with the acetabulum (socket) of the hip joint in the pelvis. To insert the implant, the head of the femur is removed and a cavity formed in the bone just below the cut. The shaft of the implant is then anchored into the cavity using, e.g., a press-fit or bone cement.

Implants made of carbon fiber embedded in a polymeric matrix have been used in place of earlier designed metal implants. Carbon fiber implants can be engineered to exhibit a stiffness (i.e., elasticity) more closely resembling that of natural bone, which has less of an adverse effect than implants exhibiting less elasticity than natural bone.

One method of making an implant of continuous carbon fiber involved stacking layers of continuous carbon fiber in which the carbon fiber in each layer was arranged in a parallel manner. The orientation of carbon fiber in the final implant could then be varied by stacking the individual layers in such a way that the fibers were aligned in the desired direction. The final product was produced by melting the polymeric matrix in which the fibers were embedded in order to cause the matrix to flow. Upon cooling, the matrix hardened into a composite block in which the various layers of carbon fiber were aligned as desired.

Fibers were aligned in these composite blocks in directions wherein increased strength was considered to provide optimum results. For example, reinforcement was provided along the shaft (i.e., longitudinal axis) by orienting a majority of the fibers in that direction. Reinforcement was also provided in the neck by orienting fibers along the neck axis, i.e., along the line formed by angle $\theta$ with the longitudinal axis, and by further providing fibers at the angle $-\theta$ to the longitudinal axis. However, it was hitherto believed that the shaft region should be more strongly reinforced than the neck region.

Accordingly, the present invention is an improved femoral implant for a hip prosthesis comprising a longitudinal shaft having a neck extending therefrom at an acute angle $\theta$ to the longitudinal direction made of layers of carbon fibers in a biocompatible polymeric matrix, each layer containing unidirectional carbon fibers and the layers arranged such that carbon fibers are oriented in the longitudinal direction and the $\pm\theta$ direction wherein at least 50% of the layers are balanced in the $\pm\theta$ direction. The femoral implant of the presently claimed invention is useful in humans and other mammals.

In accordance with the present invention, it was discovered that a composite device does not require primary reinforcement in the shaft because that part of the device is firmly supported by the femur. In fact, flexibility in the stem is important in order to permit stress transmission to the bone to forestall bone resorption. On the other hand, the neck of the device protrudes above, and at an angle to, the femur. Since the neck is not surrounded by bone, it will not benefit from bone support, and flexibility in the neck is not important as in the stem. Accordingly, the presently claimed invention takes advantage of the options available in carbon-fiber composite design by maximizing strength in the neck region and providing sufficient flexibility in the shaft region while maintaining strength in the shaft at an acceptable level.

Various types of carbon fiber are useful in accordance with the presently claimed invention. Such fibers are well known and commonly used in the manufacture of carbon fiber composite hip prostheses as disclosed in U.S. Pat. No. 4,512,038, the disclosure of which is incorporated herein by reference. The manufacture of composite materials containing layers of carbon fiber embedded in a polymeric matrix and prosthetic devices from blocks of composite material containing carbon fiber at differing angles of orientation is well known as disclosed in U.S. Pat. No. 4,892,552 and *Proc. 23rd Nat. Symp. Exhib. Adv. Mat. Process Eng*, p. 250 (1978), the disclosures of which are incorporated herein by reference. For example, a carbon fiber tow is drawn through a solution of the polymeric matrix. The coated fiber is then wound on a drum to form a single layer of the tow. Upon drying, the material on the drum is slit along the length of the drum and a coherent layer of material is unwound into a sheet. Rectangular pieces are then cut from the sheet in such a way that the fibers are oriented in the rectangle at the desired angle. A stack of the rectangles is prepared containing the desired fiber orientation, which is then heated under pressure to form a single block of the composite material.

In arranging the composite layers in accordance with the present invention it is preferable that the completed stack exhibit balance and symmetry. "Balance" means that for every layer having fibers oriented $+\theta$ to the 0° direction there is a layer having fibers oriented in the $-\theta$ direction. "Symmetry" means that the stack of layers represents two halves which are mirror images of each other. That is, the stacking sequence of the first half of the block is reversed in the second half. Preferably each block contains about 80–160 layers.

Figure 1:
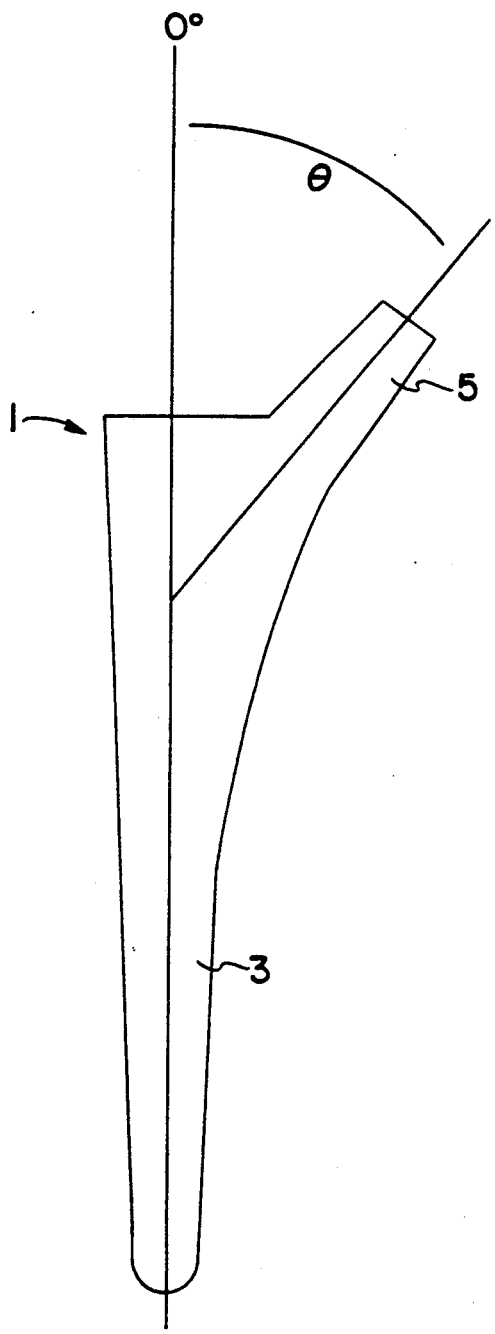
FIG. 1 is a schematic view showing the orientation of a preferred embodiment of the present invention.

With reference to FIG. 1, a preferred embodiment of the presently claimed invention is machined from a composite block of material so that implant 1 has a shaft 3 disposed in the 0° direction. Neck 5 projects at angle $\theta$ to the longitudinal direction from shaft 3. Preferably, angle $\theta$ is about 25°–55°. Accordingly, at least 50%, preferably 50–60%, of the number of layers are balanced to reinforce the neck region. That is, half of the at least 50% of the layers contain carbon fibers oriented along the neck axis and half of at least 50% of the layers contain fibers oriented so as to balance the layers oriented along the neck axis. Preferably, 20–30% of the layers contain fibers oriented in the longitudinal, or 0°, direction of the femur implant.

Figure 2:
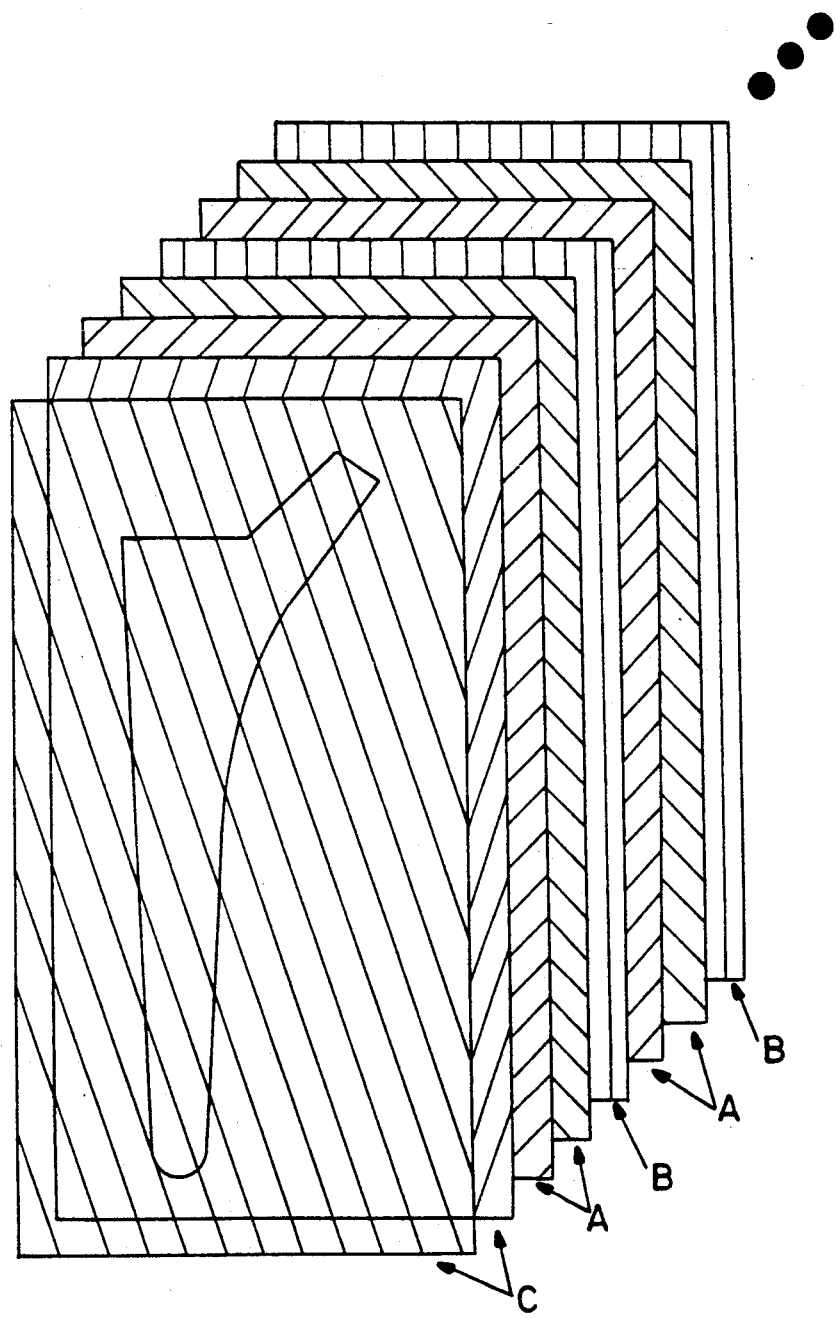
FIG. 2 is an exploded perspective view of a stage in the production of a preferred embodiment of the present invention.

With reference to FIG. 2, layer groupings A, B, and C of carbon fiber embedded in a polymeric matrix are stacked in a balanced arrangement. The A layers are balanced in the ±θ direction wherein θ is 25°–55°. The B layers contain fibers oriented in the 0° direction. The C layers are balanced in the ±β direction wherein β is 13°–23°, preferably 15°–21°. The outline of the final product appears on the foremost layer. The stack is then placed in a mold and heated under pressure in order to form a composite block of the polymer matrix in which the individual layers of fiber are contained. The composite block is then machined according to well known procedures in order to fashion the desired femoral implant, such as disclosed in the aforesaid U.S. Pat. No. 4,512,038.

The amount of polymeric matrix in the implant is sufficient to provide cohesiveness among the carbon fibers and varies depending on the number of layers in the device. Preferably polymeric content varies from 40–60% by volume, more preferably 42–48%, of the implant, with carbon fiber making up the remainder. Useful materials for the polymer matrix are biocompatible engineering thermoplastics such as disclosed in the aforesaid U.S. Pat. No. 4,892,552. Preferably, the polymer matrix is a medical grade polysulfone resin.

The size of the individual layers used to make the composite block varies depending on the size of fiber used and how much material coats the fiber. Preferably the layers are 0.1–0.5 mm thick, more preferably 0.15–0.35 mm. Sufficient layers are used to form a composite block having dimensions large enough for the femoral implant. Preferably, the block is about 15–25 mm thick.

Figure 3:
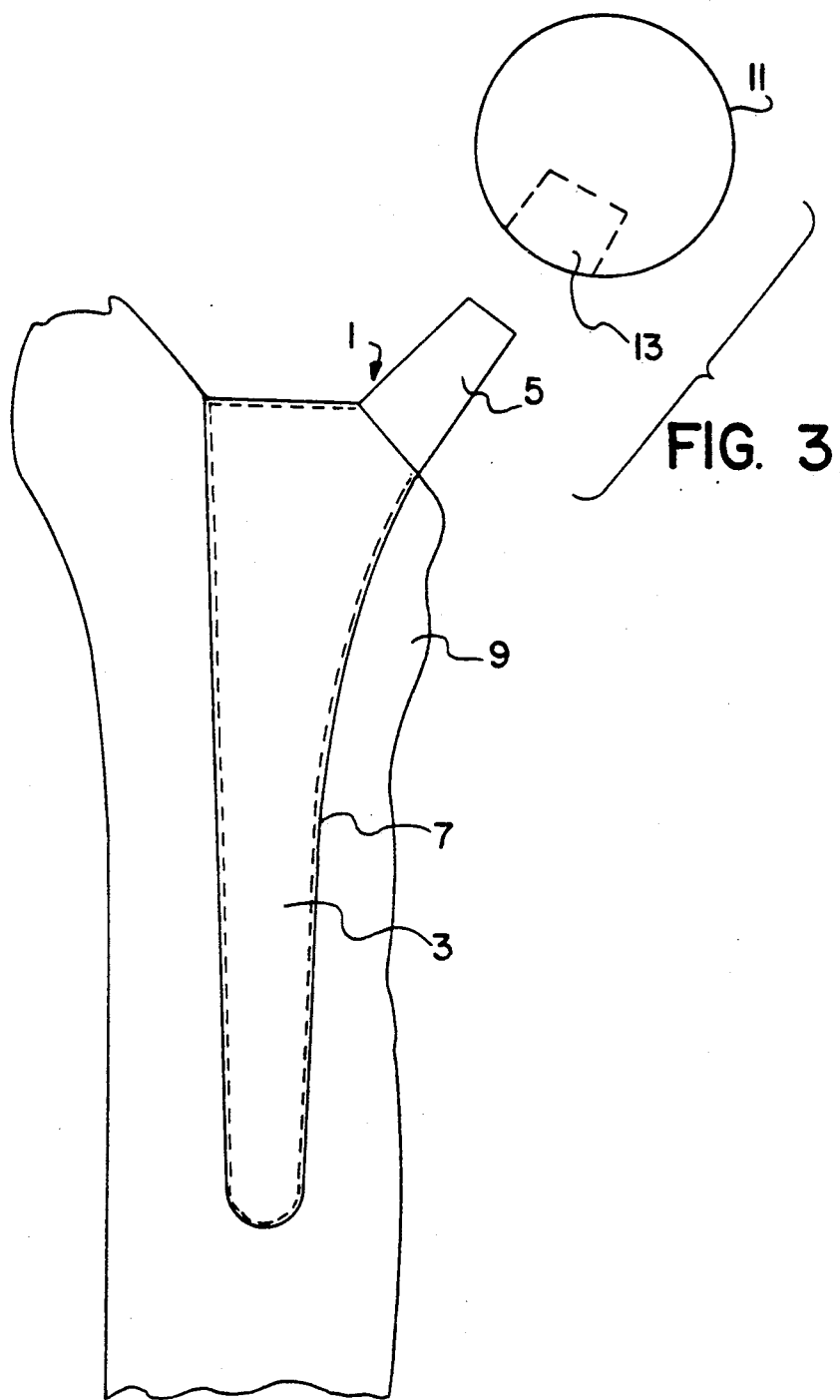
FIG. 3 is a schematic view showing the use of a preferred embodiment of the present invention.

With reference to FIG. 3, use of a preferred embodiment of the present invention is described. Shaft 3 of implant 1 is anchored in cavity 7 of femur 9. Neck 5 of implant 1 is fixed to ball 11, which is designed to cooperate with the acetabulum of the pelvis (not shown). The ball is made of known surgical alloys comprised, e.g., of titanium-aluminum-vanadium or cobalt-chromium-molybdenum, according to known methods. A slot 13 in ball 11 and the neck 5 of the implant are machined tapered (i.e., Morse taper) to mate as is well known in the art. During surgery a ball is correctly selected by the surgeon for size and press-fit onto the neck. Surgical procedures for attaching femoral implants are well known.

Preferably, the femoral implant of the present invention further contains an encapsulating layer of the polymeric matrix. This is accomplished, e.g., by vacuum thermoforming two sheets of neat polymer for placement around the composite. Vacuum thermoforming is a well known technique that will be readily applicable by the skilled artisan. Typically, this is accomplished by heating two sheets of the polymer to a sufficient temperature to make the sheets moldable. Vacuum is then used to draw the sheets into a cavity having the dimensions of either the front or back surface of the composite core plus the film thickness. When cooled, the sheets are trimmed to create preforms. A pair of preforms is then placed on either side of the composite and compressed between a mold to encapsulate the composite, each preform comprising, in effect, one-half of the encapsulating layer. Advantageously, the mold conveys a textured relief to each side of the encapsulating layer, which aids in anchoring the implant in the femur. Optionally, a physiologically acceptable radiopaque material, such as barium sulfate at about 5–10% by weight of the sheet, is contained in the encapsulating sheets. This enables positioning of the device to be more readily determined during use by X-ray photography.

In order to more clearly describe the present invention, the following non-limiting example is provided.

EXAMPLE

Carbon fiber tow containing about 12,000 fibers, each about 7 μm in diameter (available from Hercules Incorporated under the designation AS4) is drawn over rollers submerged in a solution of polysulfone resin (UDEL MG11 available from Amoco Performance Products) in methylene chloride to coat the fibers with resin. The resin-impregnated tow is taken up on a revolving polytetrafluoroethylene-coated drum (10.0–12.5" in diameter and 3' long) to form a continuous cylindrical sheet in which adjacent tow strands 0.5" wide overlap each other about 0.25". The sheet is removed from the drum when the solvent has evaporated by slitting the dried material on the drum along the drum axis to form a flat rectangular sheet about 0.25 mm thick. Rectangular coupons are cut from the sheet so as to obtain coupons having fibers oriented with respect to the length of the rectangle at 0°, +18°, −18°, +40°, and −40°.

A stack of the coupons is formed such that the length of the rectangle represents the axis of the shaft of the femoral implant, i.e., the 0° direction. Starting from the bottom of the block, the first coupon contains fibers oriented −18° relative to the 0° axis, which is followed by a layer containing fibers oriented +18°. The third and fourth layers contain fibers oriented respectively in the +40° and −40° direction. The fifth layer contains fibers oriented in the 0° direction. The sixth layer is oriented +40°, the seventh layer −40°, and the eighth layer 0°. The foregoing stacking sequence is represented according to code as follows: $[-18°, +18°, +40°, -40°, 0°, +40°, -40°, 0°]_{ns}$. The "s" denotes that the block is symmetric to its mid-plane, and the sequence is repeated "n" times to create half of the block, and then the sequence is reversed for an equal number "n." The total number of coupons in the stack varies from 80–160, depending on the desired size of the implant.

The stack of coupons is placed in a 10"×10" mold and compression molded at about 100 psi and 293° C. to form a block of the composite material. The longitudinal modulus of the composite is about 8 msi. A core femoral implant is machined from the block using well known techniques to a shape approximating that in FIG. 1. Supporting the neck of the device, 50% of the lamina are the ±40° plies. The core is then encapsulated in the same polysulfone resin used to impregnate the fibers by vacuum-thermoforming matched pairs of preforms and compression molding them to the core at 195°–200° C. for about 11 minutes.

What is claimed is:

1. In a femoral implant for a hip prosthesis comprising a shaft oriented in a longitudinal direction having a neck extending therefrom at an acute angle θ to the longitudinal direction made of layers of carbon fiber in a biocompatible polymeric matrix, each layer containing unidirectional carbon fibers and the layers arranged such that carbon fibers are oriented in the longitudinal direction and the ±θ direction, the improvement wherein at least 50% of the layers are oriented in the ±θ direction.

2. The implant of claim 1 wherein the layers are arranged symmetrically.

3. The implant of claim 1 having 50–60% of the layers oriented in the ±θ direction.

4. The implant of claim 1 having 20–30% of the layers oriented in the longitudinal direction.

5. The implant of claim 1 wherein $\theta$ is 25°–55°.

6. The implant of claim 5 further comprising layers of carbon fiber oriented ±13°–23° to the longitudinal direction.

7. The implant of claim 6 wherein the number of layers having carbon fiber oriented in the longitudinal direction equals the number of layers having carbon fiber oriented in the ±13°–23° direction.

8. In a method of using a femoral implant in hip-joint replacement surgery, wherein the implant comprises a shaft oriented in a longitudinal direction having a neck extending therefrom at an acute angle $\theta$ to the longitudinal direction made of layers of carbon fiber in a biocompatible polymeric matrix, each layer containing unidirectional carbon fibers and the layers arranged such that carbon fibers are oriented in the longitudinal direction and the ±$\theta$ direction, the improvement wherein at least 50% of the layers are oriented in the ±$\theta$ direction.

9. In a method of making a femoral implant comprising the steps of forming individual layers of unidirectional carbon fibers, stacking the layers such that carbon fibers are oriented in a longitudinal direction and ± angle $\theta$ thereto, heating the stacked layers under pressure to melt the matrix, which upon cooling forms a composite block, and machining the block into the form of the implant having a neck projecting in the direction of the angle $\theta$, the improvement comprising stacking the layers such that at least 50% of the layers are oriented in the ±$\theta$ direction.

10. The implant of claim 1 wherein the layers are oriented in the ±$\theta$ direction so that the number of layers in the +$\theta$ direction equals the number of layers in the −$\theta$ direction.

11. The implant of claim 1, having layers arranged in repeating units, each unit comprising layers oriented in sequence +$\theta$, −$\theta$, 0, +$\theta$, −$\theta$, 0, where 0 is the longitudinal direction.

12. The implant of claim 1, having a mid plane with an equal number of repeating units of layers on each side thereof, each unit comprising layers oriented in sequence approaching the mid plane of +$\theta$, −$\theta$, 0, +$\theta$, −$\theta$, 0, where 0 is the longitudinal direction.

13. The implant of claim 1, further comprising layers of carbon fiber oriented in the ±$\beta$ direction, wherein $\beta$ is 13°–23° to the longitudinal direction, and wherein the layers are arranged in repeating units, each unit comprising layers oriented in sequence −$\beta$, +$\beta$, +$\theta$, −$\theta$, 0, +$\theta$, −$\theta$, 0, where 0 is the longitudinal direction.

14. The implant of claim 1, further comprising layers of carbon fiber oriented in the ±$\beta$ direction, wherein $\beta$ is 13°–23° to the longitudinal direction, and having a mid plane with an equal number of repeating units of layers on each side thereof, each unit comprising layers oriented in sequence approaching the mid plane of −$\beta$, +$\beta$, +$\theta$, −$\theta$, 0, +$\theta$, −$\theta$, 0, where 0 is the longitudinal direction.

* * * * *